US011506595B2

(12) United States Patent
Vos et al.

(10) Patent No.: US 11,506,595 B2
(45) Date of Patent: Nov. 22, 2022

(54) NON-CONTACT TORQUE SENSING (71) Applicant: Halliburton Energy Services, Inc., Houston, TX (US)

(72) Inventors: Andrew D. Vos, Spring, TX (US); Dale E. Jamison, Humble, TX (US); Ketan C. Bhaidasna, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 563 days.

(21) Appl. No.: 16/611,443

(22) PCT Filed: Dec. 18, 2018

(86) PCT No.: PCT/US2018/066269
§ 371 (c)(1),
(2) Date: Nov. 6, 2019

(87) PCT Pub. No.: WO2020/131038
PCT Pub. Date: Jun. 25, 2020

(65) Prior Publication Data
US 2021/0055203 A1 Feb. 25, 2021

(51) Int. Cl.
*G01N 19/02* (2006.01)
*E21B 21/00* (2006.01)
(Continued)

(52) U.S. Cl.
CPC ............ *G01N 19/02* (2013.01); *E21B 21/00* (2013.01); *G01L 3/08* (2013.01); *G01N 33/2823* (2013.01); *G01N 33/30* (2013.01)

(58) Field of Classification Search
CPC ................................ G01N 11/14; G01N 19/02
See application file for complete search history.

(56) References Cited

U.S. PATENT DOCUMENTS 4,175,425 A * 11/1979 Brookfield ............. G01N 11/14
73/54.35
5,052,219 A 10/1991 Fery et al.
(Continued)

FOREIGN PATENT DOCUMENTS

CN 104034462 9/2014

OTHER PUBLICATIONS

ISRWO International Search Report and Written Opinion for PCT/US2018/066269 dated Sep. 18, 2019.

*Primary Examiner* — Paul M. West
*Assistant Examiner* — Mark A Shabman
(74) *Attorney, Agent, or Firm* — Tenley Krueger; C. Tumey Law Group PLLC (57) ABSTRACT

A lubricity tester unit may comprise a housing, a shaft, wherein a first end of the shaft is disposed at a first end of the housing, wherein the shaft extends through housing along a central axis of the housing, and an encoder, wherein the encoder is disposed on an internal wall of the housing, wherein the shaft is disposed through a hole in the encoder, wherein the encoder is an optical encoder configured to measure angular position of the shaft. The lubricity tester unit may further comprise rotating rings, wherein the rotating rings are coupled to a second end of the shaft, a friction inducing surface, wherein the friction inducing surface is disposed around the rotating rings, a first sensor, wherein the first sensor is disposed through the housing, and a second sensor, wherein the second sensor is disposed through the housing.

20 Claims, 7 Drawing Sheets

(51) Int. Cl.
*G01L 3/08* (2006.01)
*G01N 33/28* (2006.01)
*G01N 33/30* (2006.01)

(56) References Cited

U.S. PATENT DOCUMENTS

| | | | |
|---|---|---|---|
| 5,616,842 A * | 4/1997 | Armengaud | G01N 33/2823 73/53.05 |
| 5,616,845 A | 4/1997 | Hickling et al. | |
| 6,105,415 A | 8/2000 | Kenney | |
| 6,318,187 B1 | 11/2001 | Griepentrog et al. | |
| 7,024,920 B2 | 4/2006 | Discenzo | |
| 9,194,784 B1 | 11/2015 | Bi et al. | |
| 9,528,974 B2 | 12/2016 | Livescu et al. | |
| 2003/0145663 A1* | 8/2003 | Heisenberg | G01L 3/12 73/862.324 |
| 2011/0015878 A1 | 1/2011 | LaVigne et al. | |

* cited by examiner

NON-CONTACT TORQUE SENSING

BACKGROUND

Wells may be drilled at various depths to access and produce oil, gas, minerals, and other naturally-occurring deposits from subterranean geological formations. Wells may also be drilled in a variety of environments, including in deep water where ocean floor conditions may be softer or more unconsolidated as desired when drilling. Frictional resistance to rotation of the drill string and to hoisting and lowering the drill string may be affected by the drilling fluid utilized. Many different materials have been used as drilling fluid additives to improve lubricity, thereby reducing friction.

The lubricity of a given drilling fluid may be a property of special importance in drilling directional wells. An increase in friction between drill string and borehole may be expected when drilling a directional hole that is off-vertical. Most wells drilled from fixed platforms offshore may be completed in deviated holes. Desirable characteristics of a lubricant for this purpose, aside from the requirement of performing well as a lubricant, may be that the lubricant is non-toxic, biodegradable, and does not form an oily slick on water.

Often evaluation of the various lubricating materials in the various types and quality of drilling fluid may not be performed on the drilling rig, so a functional drilling fluid lubricity tester unit may be used off-site to simulate the torque and drag produced by a given drilling fluid downhole. The tester unit may model or approximate the speed of rotation of the drill pipe and the pressure with which the pipe bears against the wall of the hole where friction may be generated.

Typically, such tester units may rely on a method of operation wherein additional contact points are introduced into the system. These contact points may add error to the measurements as additional friction is produced. In other examples, electromagnetic sensors may be used. In these examples, additional filtering may be required and the measurements may be affected by the surrounding temperature.

BRIEF DESCRIPTION OF THE DRAWINGS

These drawings represent certain aspects of the present invention and should not be used to limit or define the disclosure.

DETAILED DESCRIPTION

The present examples relate to processes involved with subterranean operations and, more particularly, to the lubricity of drilling fluids. Disclosed herein are design features that may be beneficial over current available lubricity tester units, such as the use of optical sensors. In examples, the optical sensors may measure the angular displacement of the ends of a rotating shaft, wherein the rotating shaft is disposed in a pressure vessel. In these examples, a motor may operate to cause the shaft to rotate against a friction inducing surface.

Figure 1:
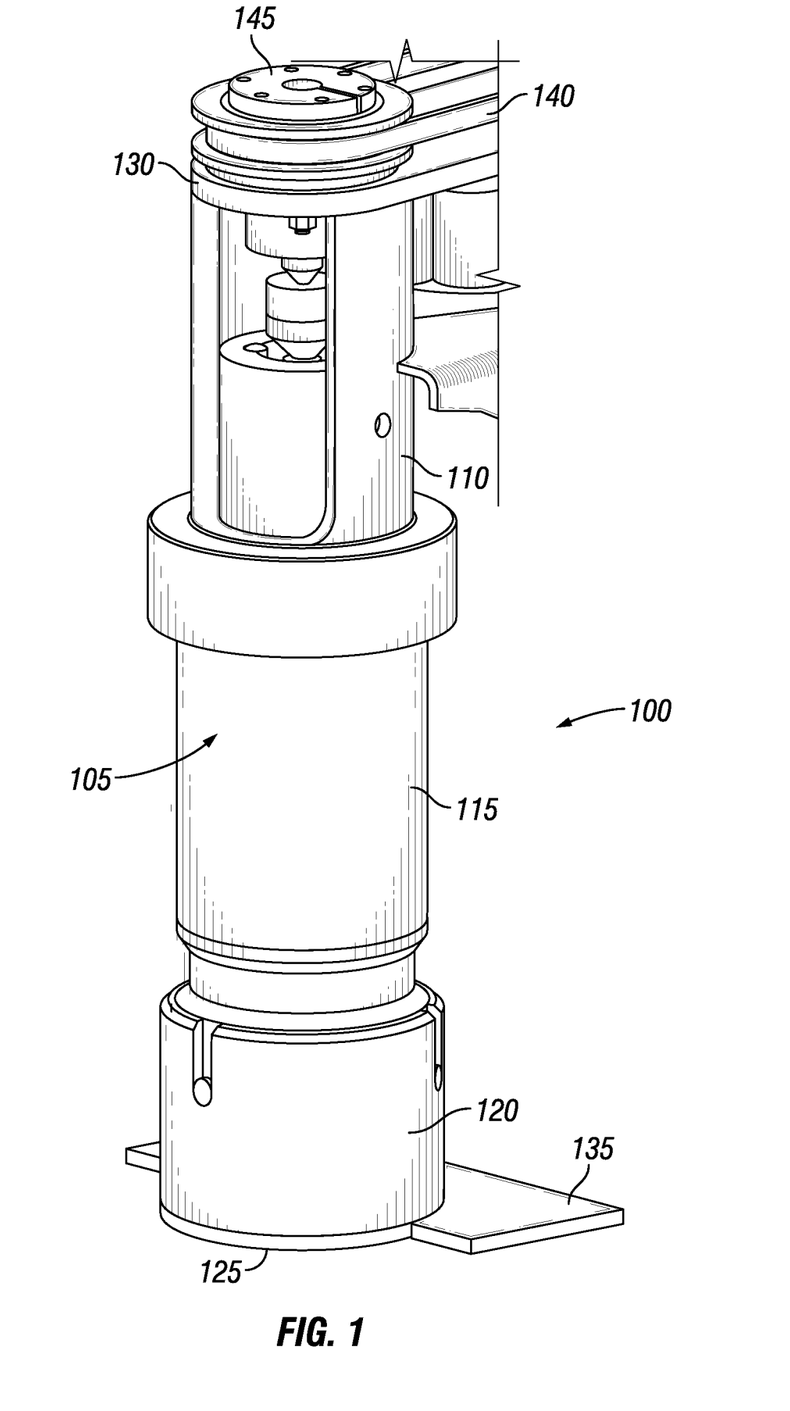
FIG. 1 illustrates an example of a lubricity tester unit.

FIG. 1 illustrates an example of a lubricity tester unit 100. Lubricity tester unit 100 may be used to determine the lubricity of a drilling fluid. As used herein, "lubricity" is defined as the measure of the reduction in friction and/or wear. Lubricity tester unit 100 may include a housing 105 and a motor (not illustrated). During operations, a drilling fluid may be disposed within housing 105. Once contained within housing 105, lubricity tester unit 100 may operate to determine the lubricity of the drilling fluid. Housing 105 may be any suitable size, height, and/or shape. Without limitation, a suitable shape may include, but is not limited to, cross-sectional shapes that are circular, elliptical, triangular, rectangular, square, hexagonal, and/or combinations thereof. In examples, housing 105 may be cylindrical. Without limitation, housing 105 may include any suitable material such as metals, nonmetals, polymers, ceramics, and/or any combination thereof. Housing 105 may be an external structure that includes internal components that may operate in a pressurized environment. Housing 105 may include a top sub assembly 110, a coupling sub assembly 115, and a bottom sub assembly 120. Top sub assembly 110, coupling sub assembly 115, and bottom sub assembly 120 may have similar shapes and/or dimensions, as shown, or may have different shapes and/or dimensions as desired for a particular application. Coupling sub assembly 120 may serve to join top sub assembly 110 to bottom sub assembly 120. Collectively, top sub assembly 110, coupling sub assembly 115, and bottom sub assembly 120 may be open to each other and allow material to travel throughout housing 105. In other examples, top sub assembly 110, coupling sub assembly 115, and/or bottom sub assembly 120 may be separated or closed-off from each other.

Housing 105 may further include a first end 125 and a second end 130. In examples, first end 125 and/or second end 130 may be closed in relation to housing 105 in order for housing 105 to be a closed container. First end 125 may be the distal end of bottom sub assembly 120 and may be disposed onto an external base 135. In examples, external base 135 may be any suitable surface on which lubricity tester unit 100 may be disposed upon. Without limitations, external base 135 may be a surface in a laboratory environment and/or rig equipment at the surface of a wellbore. First end 125 may be disposed onto external base 135 through the use of any suitable mechanisms, including, but not limited to, the use of suitable fasteners, threading, adhesives, welding, and/or combinations thereof. Without limitation, suitable fasteners may include nuts and bolts, washers, screws, pins, sockets, rods and studs, hinges and/or any combination thereof.

Second end 130 may be the proximal end of top sub assembly 110 and may be coupled to the motor (not illustrated). In examples, a belt drive 140 may couple second end 130 to the motor. Belt drive 140 may transfer rotational energy from the motor to lubricity tester unit 100 at second end 130. As illustrated, a pulley 145 may be disposed at second end 130. Without limitations, pulley 145 may be a wheel with a grooved rim. Belt drive 140 may be disposed around pulley 145 in the grooved rim and actuated to cause pulley 145 to rotate as the motor operates. Without limitations, pulley 145 may rotate at an angular speed greater than, equal to, or less than the operating speed of the motor.

Figure 2:
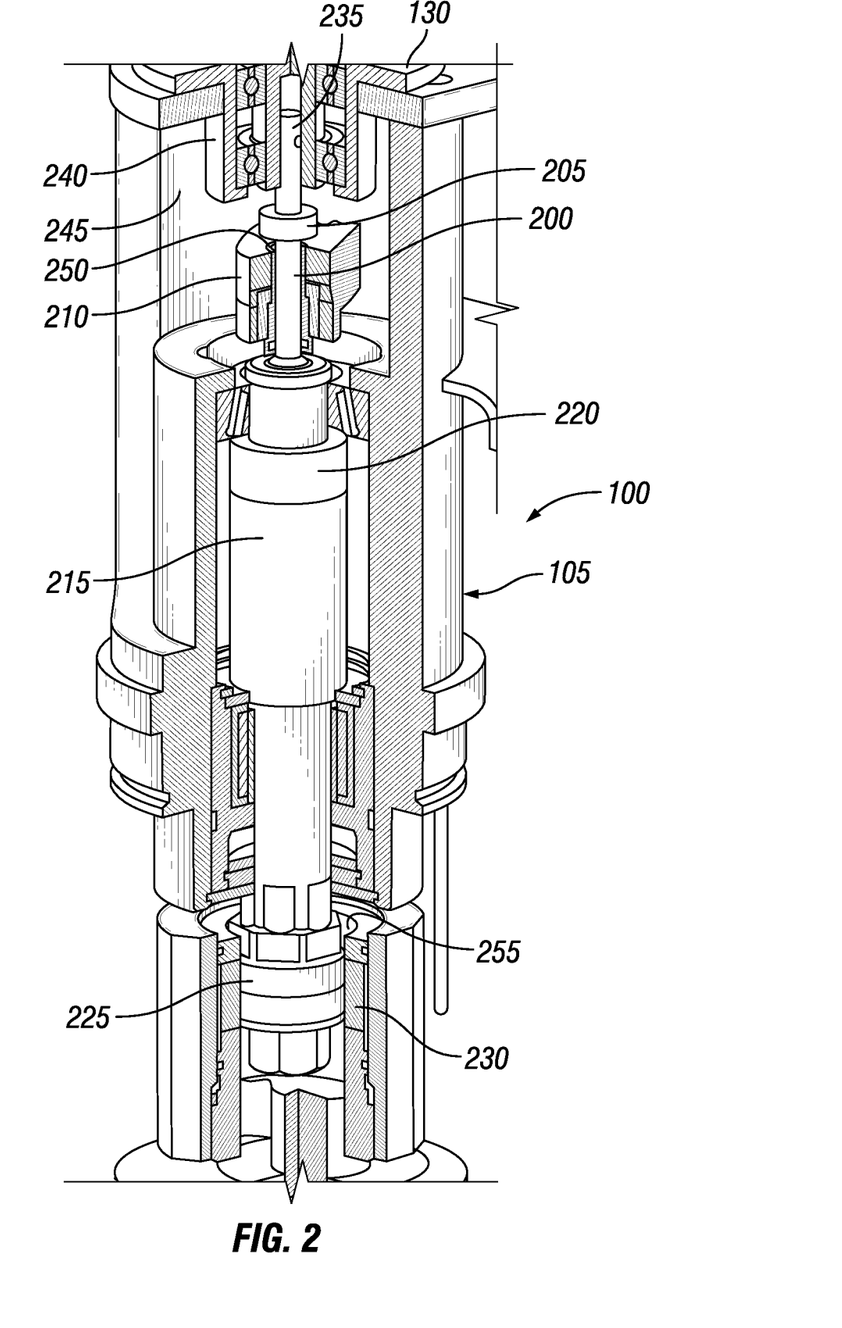
FIG. 2 illustrates a cross-sectional, isometric view of a housing of an example lubricity tester unit.

FIG. 2 illustrates a cross-sectional, isometric view of lubricity tester unit 100. As illustrated, lubricity tester unit 100 may further include a shaft 200, a first flag 205, an encoder 210, a sleeve 215, a second flag 220, rotating rings 225, and a friction inducing surface 230 disposed within housing 105. Shaft 200 may be any suitable size, height, and/or shape. Without limitation, a suitable shape may include, but is not limited to, cross-sectional shapes that are circular, elliptical, triangular, rectangular, square, hexagonal, and/or combinations thereof. In examples, shaft 200 may generally be an elongated, rigid rod. Without limitation, shaft 200 may include any suitable material such as metals, nonmetals, polymers, ceramics, and/or any combination thereof. In examples, a first end 235 of shaft may be coupled to pulley 145. As illustrated, pulley 145 may include a protruding extension 240 that extends perpendicular from pulley 145. Protruding extension 240 may be a hollow tubular configured to receive first end 235 of shaft 200. First end 235 of shaft may be disposed into and secured to protruding extension 240 through the use of any suitable mechanisms, including, but not limited to, the use of suitable fasteners, threading, adhesives, welding, and/or combinations thereof. Without limitation, suitable fasteners may include nuts and bolts, washers, screws, pins, sockets, rods and studs, hinges and/or any combination thereof. As pulley 145 rotates, shaft 200 may rotate accordingly. In examples, there may be other components of lubricity tester unit 100 disposed onto shaft 200 in order to acquire measurements of shaft 200 during operation of lubricity tester unit 100. Without limitations, first flag 205, encoder 210, sleeve 215, second flag 220, and/or combinations thereof may be disposed on shaft 200.

First flag 205 and second flag 220 may be any suitable size, height, and/or shape. Without limitation, a suitable shape may include, but is not limited to, cross-sectional shapes that are circular, elliptical, triangular, rectangular, square, hexagonal, and/or combinations thereof. First flag 205 and second flag 220 may serve as markers to designate a position of shaft 200. Without limitation, first flag 205 and second flag 220 may include any suitable material such as metals, nonmetals, polymers, ceramics, and/or any combination thereof. In examples, first flag 205 and second flag 220 may have a reflective surface. In other examples, first flag 205 and second flag 220 may include both reflective and non-reflective surfaces. As illustrated, first flag 205 may be disposed onto shaft 200 near first end 235, wherein shaft 200 aligns with the central axis of first flag 205. Further, second flag 220 may be disposed on an external surface of sleeve 215 so as to align perpendicularly with first flag 205. During operations, as shaft 200 experiences torque, second flag 220 may lag timewise behind first flag 205. The time difference between second flag 220 and first flag 205 may be proportional to the stiffness and torque of shaft 200. During operations of lubricity tester unit 100, first flag 205 and/or second flag 220 may be used concurrently with encoder 210, wherein encoder 210 may track the angular location of shaft 200.

Encoder 210 may be a device configured to measure the angular position and/or motion of shaft 200 as electrical signals. In examples, encoder 210 may be an absolute encoder or an incremental encoder. Without limitations, encoder 210 may be conductive, optical, on-axis magnetic, off-axis magnetic, and/or combinations thereof. In the present example, encoder 210 may be an optical encoder. Encoder 210 may be any suitable size, height, and/or shape.

Encoder 210 may be mounted about an internal wall 245 of housing 105 and extend inward towards the central axis of housing 105. Encoder 210 may include a hole 250 traversing through the thickness of encoder 210. Hole 250 may be configured to receive shaft 200. In examples, the diameter of hole 250 may be greater than the diameter of shaft 200. As shaft 200 rotates, encoder 210 may measure and record the angular position of shaft 200. Encoder 210 may digitize the angular position of shaft 200 into electrical signals that allow an operator to measure displacement and/or speed of shaft 200. Without limitations, encoder 210 may employ any suitable technologies such as, without limitation, optical, magnetic, mechanically conductive, and/or combinations thereof. In examples, encoder 210 may be disposed between first flag 205 and sleeve 215.

Sleeve 215 may be a hollow tubular disposed around shaft 200. As illustrated, shall 200 may be disposed through sleeve 215 and run along the central axis of sleeve 215, in examples, sleeve 215 may be any suitable size, height, and/or shape and may be made from any suitable material. Sleeve 215 may serve to seal a portion of shaft 200 off from the drilling fluid present within housing 105. Sleeve 215 may subsequently protect the fastening mechanism that couples shaft 200 to rotating rings 225. Shaft 200 may be coupled to rotating rings 225 through the use of any suitable mechanisms, including, but not limited to, the use of suitable fasteners, threading, adhesives, welding, and/or combinations thereof. Without limitation, suitable fasteners may include nuts and bolts, washers, screws, pins, sockets, rods and studs, hinges and/or any combination thereof. In examples, shaft 200 is threaded to rotating rings 225.

Rotating rings 225 may be structures disposed at an end of shaft 200 opposite of first end 235. In examples, rotating rings 225 may abut against sleeve 215. In certain examples, there may be a singular rotating ring 225 rather than a plurality of rotating rings 225. Rotating rings 225 may be any suitable size, height, and/or shape. Without limitation, a suitable shape may include, but is not limited to, cross-sectional shapes that are circular, elliptical, triangular, rectangular, square, hexagonal, and/or combinations thereof. In examples, rotating rings 225 may have a circular cross-section. Without limitation, rotating rings 225 may include any suitable material such as metals, nonmetals, polymers, ceramics, and/or any combination thereof. As shaft 200 rotates, rotating rings 225 may rotate accordingly. During operations, rotating rings 225 may rub against friction inducing surface 230 as rotating rings 225 rotate.

Friction inducing surface 230 may serve to press against rotating rings 225 and produce a reaction torque due to friction acting against shaft 200. Without limitation, friction inducing surface 230 may include any suitable material such as metals, nonmetals, polymers, ceramics, rock, simulated rock, simulated permeable material, non-permeable material, and/or any combination thereof. In examples, friction inducing surface 230 may be disposed about internal wall 245 of housing 105 and surround rotating rings 225. Friction inducing surface 230 may have a hollow, circular cross-section wherein rotating rings 225 are suspended within the hollow space of friction inducing surface 230. As lubricity tester unit 100 operates, friction inducing surface 230 may be displaced so that an internal wall 255 of friction inducing surface 230 comes into contact with rotating rings 225. As rotating rings 225 rotate due to the rotation of shaft 200, friction inducing surface 230 may apply a reaction torque to rotating rings 225 in the direction opposite that of the direction of motion. Since rotating rings 225 are coupled to shaft 200, the reaction torque may be transferred and applied to shaft 200 where rotating rings 225 are coupled to shaft 200.

Figure 3:
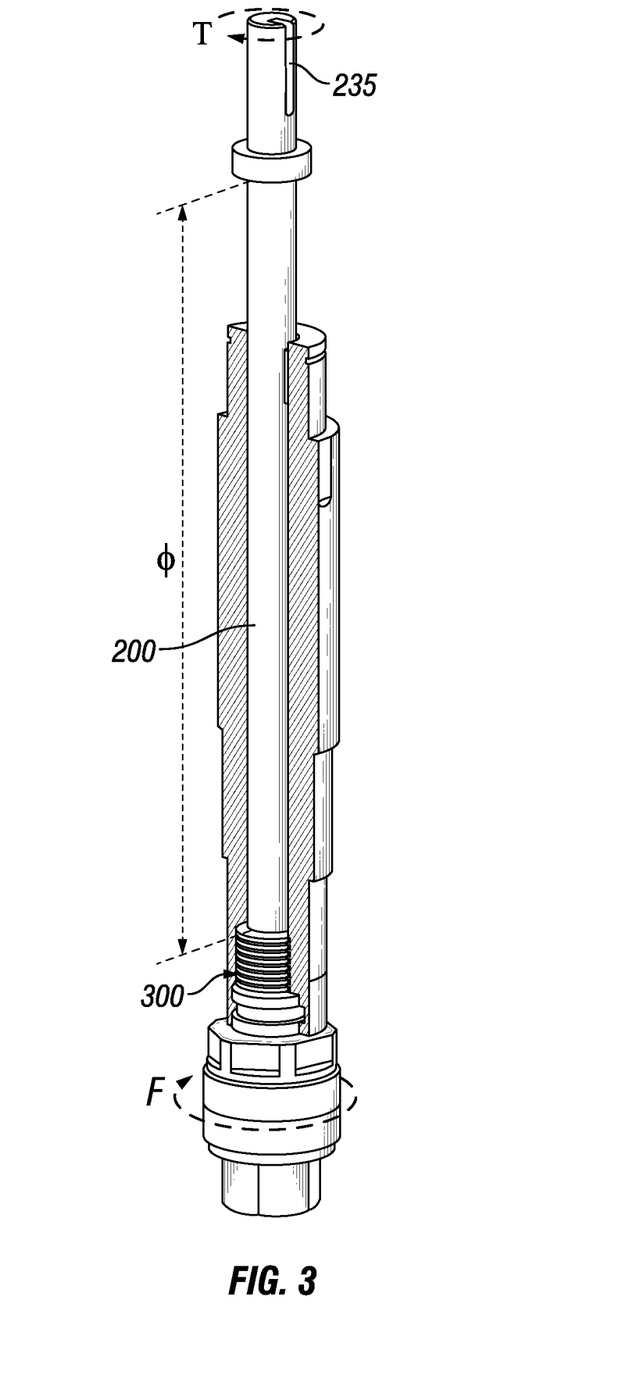
FIG. 3 illustrates a cross-sectional, isometric view of the internal components within a housing of an example lubricity tester unit.

The reaction torque may be necessary in producing an angular displacement between first end 235 and an opposing end of shaft 200. With reference now to FIG. 3, the angular displacement between first end 235 and second end 300 of shaft 200 may be designated as φ (phi). In examples, encoder 210 (i.e., referring to FIG. 2), along with other components discussed below, may be able to measure the angular displacement. In certain conditions, the torque supplied by the motor would not cause angular displacement. As there is angular displacement, it may be assumed that the torque providing the angular displacement is the reaction torque supplied by friction inducing surface 230 (i.e., referring to FIG. 2). As torque is related to force, the friction force provided by friction inducing surface 230, and subsequently the coefficient of friction, may be determined from the angular displacement measurements.

Figure 4:
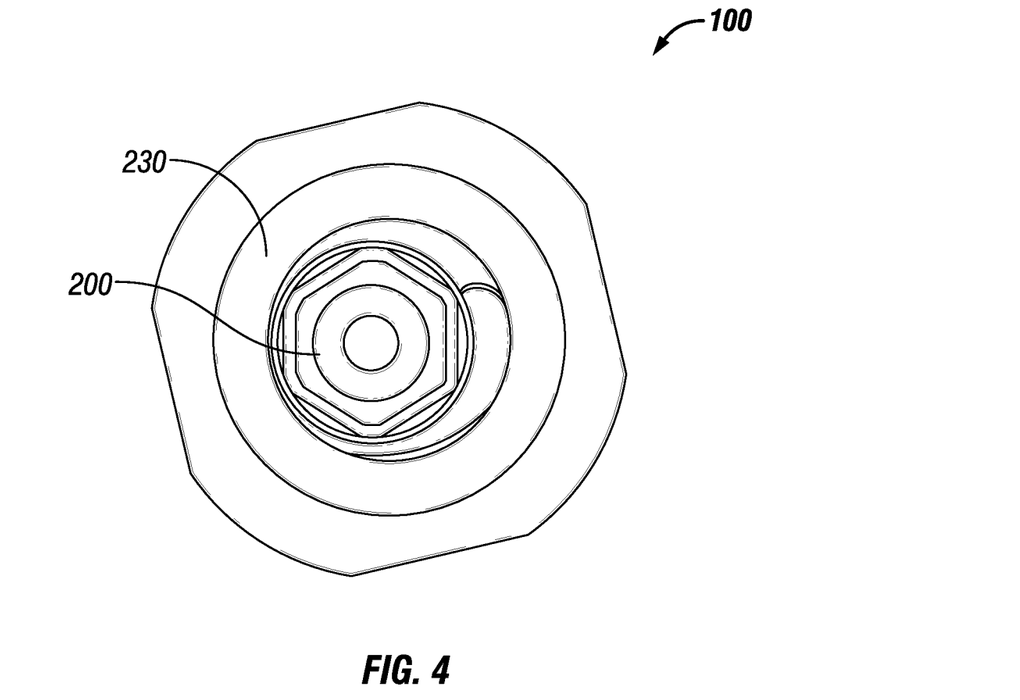
FIG. 4 illustrates a top view of a shaft rotating in an example lubricity tester unit.
Figure 5:
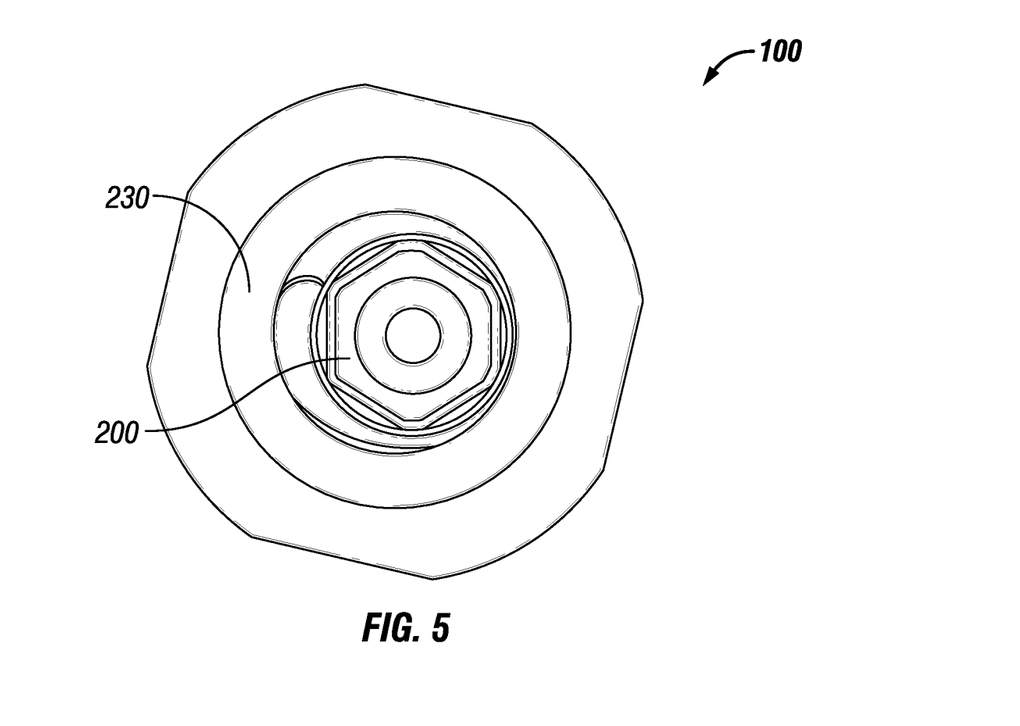
FIG. 5 illustrates a top view of a shaft rotating in an example lubricity tester unit

FIGS. 4 and 5 illustrate a top view of shaft 200 rotating in lubricity tester unit 100. As illustrated, as shaft 200 rotates, rotating rings 225 (i.e., referring to FIG. 2) may rub against friction inducing surface 230. The reaction torque produced may be transferred to shaft 200. As lubricity tester unit 100 operates, the reaction torque may be used to determine the coefficient of friction between rotating rings 225 and friction inducing surface 230. Concerning the present disclosure, the coefficient of friction may be a dimensionless, scalar ratio of the force of friction between two structures and the force acting normal to the direction of movement between the two structures. As a drilling fluid may be present within lubricity tester unit 100, the characteristics of the drilling fluid may affect the coefficient of friction. Acquiring various measurements at differing parameters may help determine the lubricity of a given drilling fluid as the observed coefficient of friction varies.

Figure 6:
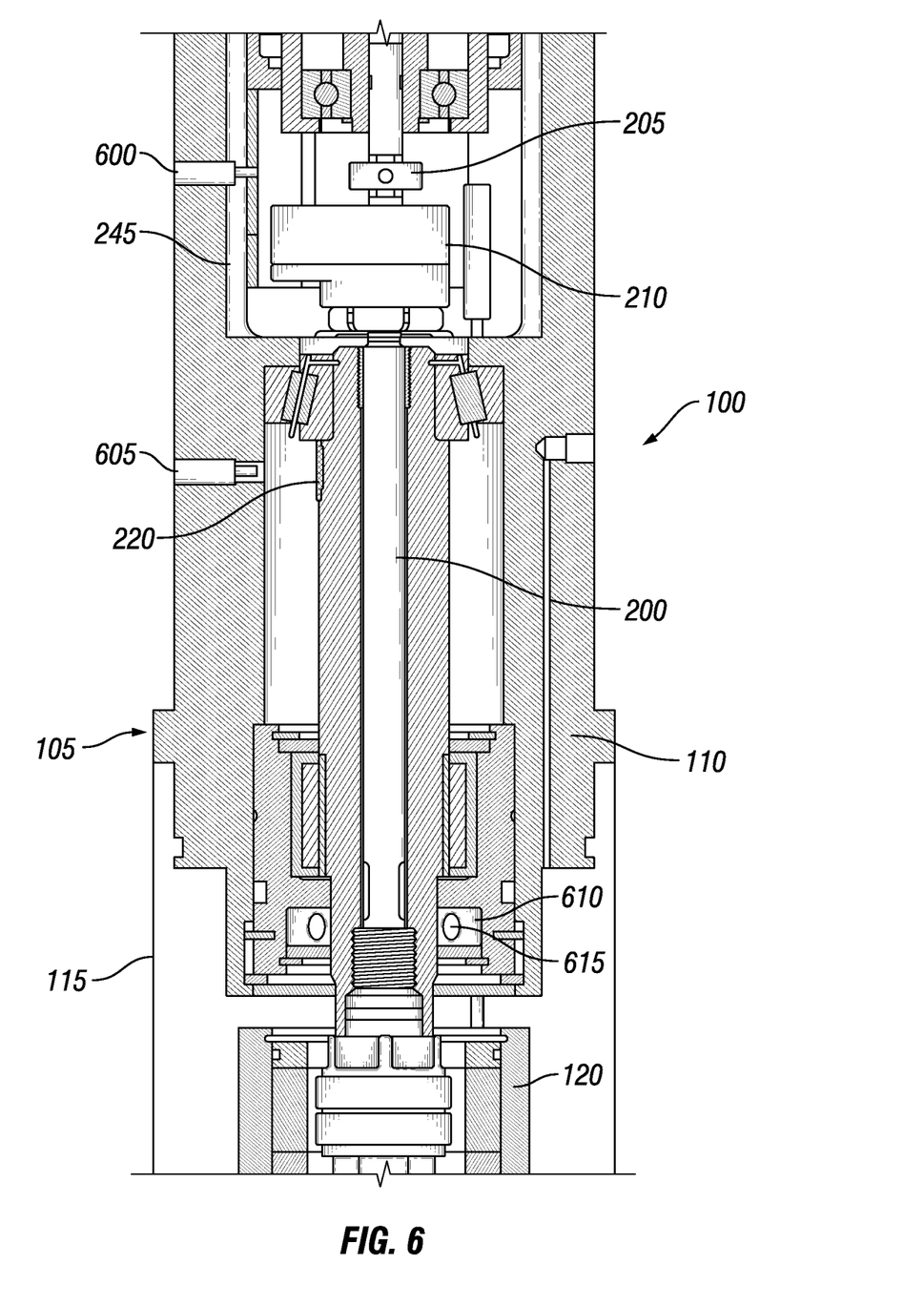
FIG. 6 illustrates a cross-sectional view of a portion of a housing of an example lubricity tester unit.

FIG. 6 illustrates a cross-sectional view of lubricity tester unit 100 further including other components. As illustrated, lubricity tester unit 100 may further include a first sensor 600 and a second sensor 605. In examples, first sensor 600 and second sensor 605 may be the same type of sensor measuring similar variables or different types of sensors measuring different variables. Without limitations, first sensor 600 and/or second sensor 605 may be Hall effect sensors, ultrasonic sensors, magnetic sensors, electrical contact sensors, and/or combinations thereof. In the present examples, first sensor 600 and second sensor 605 may be optical sensors that include a light source (not illustrated) and detector (not illustrated). First sensor 600 and/or second sensor 605 may be configured to emit light through the light source and detect reflected light through the detector. First sensor 600 and/or second sensor 605 may be any suitable size, height, and/or shape. First sensor 600 may be disposed through top sub assembly 110 of housing 105 and may at least partially extend inward towards the central axis of housing 105 past internal wall 245. In examples, first sensor 600 may align in a horizontal plane with first flag 205. Second sensor 605 may be disposed through top sub assembly 110 of housing 105 and may align in a horizontal plane with second flag 220. During operations of lubricity tester unit 100, first sensor 600 may emit light and measure the light reflected off of first flag 205 as first flag 205 rotates. Additionally, second sensor 605 may emit light and measure the light reflected off of second flag 220 as second flag 220 rotates. First sensor 600 and second sensor 605 may operate in conjunction with encoder 210 to measure both the position and angle of shaft 200 as shaft 200 rotates.

As illustrated, coupling sub assembly 115 may couple top sub assembly 110 to bottom sub assembly 120. Top sub assembly 110 may be coupled to bottom sub assembly 120 through the use of any suitable mechanisms, including, but not limited to, the use of suitable fasteners, threading, adhesives, welding, and/or combinations thereof. Without limitation, suitable fasteners may include nuts and bolts, washers, screws, pins, sockets, rods and studs, hinges and/or any combination thereof. In examples, a rotary seal 610 and O-ring 615 may be disposed between top sub assembly 110 and coupling sub assembly 115.

Figure 7:
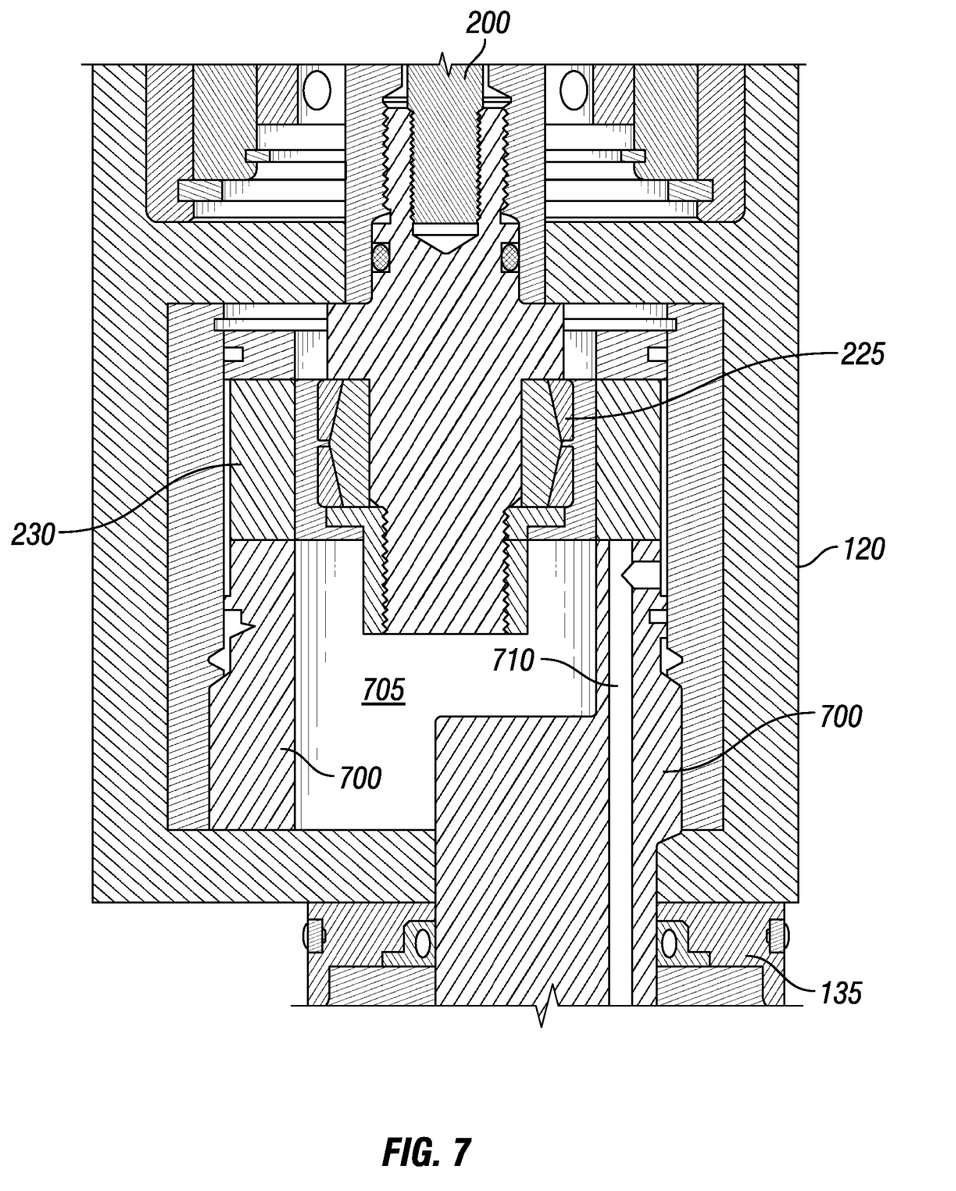
FIG. 7 illustrates a cross-sectional view of a portion of a housing of an example lubricity tester unit and FIG. 8 illustrates an example of a lubricity tester unit at the surface of a wellbore.

With reference now to FIG. 7, bottom sub assembly 120 may include a friction inducing apparatus 700, and internal chamber 705, and a fluid pathway 710. Friction inducing apparatus 700 may be any suitable structure capable of displacing friction inducing surface 230, wherein friction inducing surface may be disposed on friction inducing apparatus 700. Friction inducing apparatus 700 may be any suitable size, height, and/or shape. Without limitation, a suitable shape may include, but is not limited to, cross-sectional shapes that are circular, elliptical, triangular, rectangular, square, hexagonal, and/or combinations thereof. Without limitation, friction inducing apparatus 700 may include any suitable material such as metals, nonmetals, polymers, ceramics, and/or any combination thereof. In examples, friction inducing apparatus 700 may be disposed about an internal portion of bottom sub assembly 120. During operations, friction inducing apparatus 700 may be actuated to move and/or rotate as lubricity tester unit 100 (i.e., referring to FIG. 1) operates. In examples, friction inducing apparatus 700 may include an off-center axis in relation to lubricity tester unit 100. As friction inducing apparatus 700 is actuated, friction inducing surface 230 may be displaced to come into contact with rotating rings 225 as rotating rings 225 may be suspended along the central axis of lubricity tester unit 100 and horizontal with friction inducing surface 230.

In examples, a drilling fluid may be disposed within bottom sub assembly 120 in internal chamber 705, wherein internal chamber 705 may be defined by the friction inducing apparatus 700. During operations, as shaft 200 rotates, and subsequently as rotating rings 225 rotate, the drilling fluid may undergo physical and/or chemical effects when disposed between rotating rings 225 and friction inducing surface 230. In examples, temperature and/or pressure changes within lubricity tester unit 100 may enhance these effects. Without limitations, a reaction torque may be applied to shaft 200 due to the properties of the drilling fluid present between rotating rings 225 and friction inducing surface 230. As previously discussed, first sensor 600 (i.e., referring to FIG. 6), second sensor 605 (i.e., referring to FIG. 6), encoder 210 (i.e., referring to FIG. 2), and/or combinations thereof may analyze this reaction torque to determine the coefficient of friction of the drilling fluid.

During and/or after operation of lubricity tester unit 100, the drilling fluid may traverse through fluid pathway 710 to exit lubricity tester unit 100. Fluid pathway 710 may be any suitable path that a potential fluid may take. In examples, fluid pathway 710 may be any suitable size, height, and/or shape. Fluid pathway 710 may be disposed in friction inducing apparatus 700 and may lead to external base 135. The drilling fluid may be removed and/or further processed external to lubricity tester unit 100.

Figure 8:
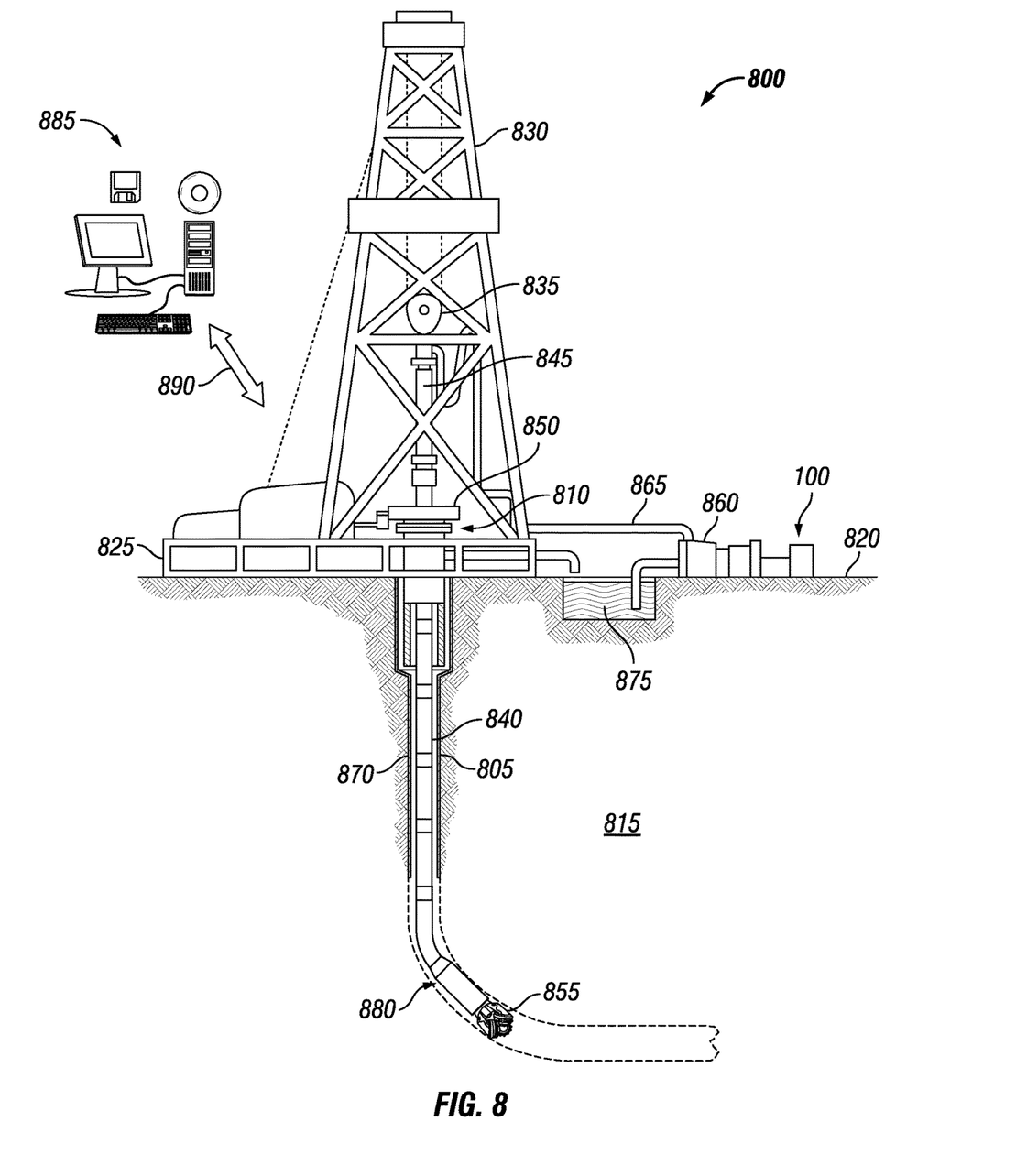

FIG. 8 illustrates an example of lubricity tester unit 100 included in a drilling system 800. As illustrated, a wellbore 805 may extend from a wellhead 810 into a subterranean formation 815 from a surface 820. A drilling platform 825 may support a derrick 830 having a traveling block 835 for raising and lowering a drill string 840. Drill string 840 may include, but is not limited to, drill pipe and/or coiled tubing, as generally known to those skilled in the art. A kelly 845 may support drill string 840 as it may be lowered through a rotary table 850. A drill bit 855 may be attached to the distal end of drill string 840 and may be driven either by a downhole motor and/or via rotation of drill string 840 at surface 820. Without limitation, drill bit 855 may include roller cone bits, PDC bits, natural diamond bits, any hole openers, reamers, coring bits, and/or the like. As drill bit 855 rotates, it may create and extend wellbore 805 to penetrate various subterranean formations 815. A pump 860 may circulate drilling fluid through a feed pipe 865 to kelly 845, downhole through the interior of drill string 840, through orifices in drill bit 855, back to surface 820 via an annulus 870 surrounding drill string 840, and into a retention pit 875.

In embodiments, drill bit 855 may be a part of a bottom hole assembly 880 at the distal end of drill string 840. As will be appreciated by those of ordinary skill in the art, bottom hole assembly 880 may be a measurement-while drilling (MWD) and/or logging-while-drilling (LWD) system. Without limitation, bottom hole assembly 880 may be connected to and/or controlled by an information handling system 885, which may be disposed on surface 820. Alternatively, information handling system 885 may be disposed downhole in bottom hole assembly 880. Processing of information recorded may occur downhole and/or on surface 820. Processing occurring downhole may be transmitted to surface 820 to be recorded, observed, and/or further analyzed. Additionally, information recorded on information handling system 885 that may be disposed downhole may be stored until bottom hole assembly 880 may be brought to surface 820. In examples, information handling system 885 may communicate with bottom hole assembly 880 through any suitable technique. Any suitable technique used for transmitting signals from bottom hole assembly 880 to surface 820, may include, but is not limited to, wired pipe telemetry, mud-pulse telemetry, acoustic telemetry, and electromagnetic telemetry. While not illustrated, bottom hole assembly 880 may include a telemetry subassembly that may transmit telemetry data to surface 820. Without limitation, an electromagnetic source in the telemetry subassembly may be operable to generate pressure pulses in the drilling fluid that propagate along the fluid stream to surface 820. At surface 820, pressure transducers (not shown) may convert the pressure signal into electrical signals for a digitizer (not illustrated). The digitizer may supply a digital form of the telemetry signals to information handling system 885 via a communication link 890, which may be a wired or wireless link. The data may be analyzed and processed by information handling system 885.

Information handling system 885 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, information handling system 885 may include a processing unit, a network storage device, or any other suitable device and may vary in size, shape, performance, functionality, and price. Information handling system 885 may include random access memory (RAM), one or more processing resources such as a central processing unit (CPU) or hardware or software control logic, ROM, and/or other types of nonvolatile memory. Additional components of the information handling system 885 may include one or more disk drives, one or more network ports for communication with external devices as well as various input and output (I/O) devices, such as an input device (e.g., keyboard, mouse, etc.) and a video display. Information handling system 885 may also include one or more buses operable to transmit communications between the various hardware components.

Alternatively, systems and methods of the present disclosure may be implemented, at least in part, with non-transitory computer-readable media. Non-transitory computer-readable media may include any instrumentality or aggregation of instrumentalities that may retain data and/or instructions for a period of time. Non-transitory computer-readable media may include, for example, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such as wires, optical fibers, microwaves, radio waves, and other electromagnetic and/or optical carriers; and/or any combination of the foregoing.

In embodiments, information handling system 885 may be in wired and/or wireless communication with lubricity tester unit 100. With continued reference to FIG. 8, the drilling fluid used during such drilling operations may be processed by lubricity tester unit 100 disposed at surface 820. In embodiments, lubricity tester unit 100 may be in fluid communication with pump 860, feed pipe 865, retention pit 875, and/or combinations thereof. As previously discussed, lubricity tester unit 100 may measure the lubricity of the drilling fluid indirectly by measuring the position and angle of the ends of shaft 200 (i.e., referring to FIG. 2) with first sensor 600 (i.e., referring to FIG. 6), second sensor 605 (i.e., referring to FIG. 6), encoder 210 (i.e., referring to FIG. 2), and/or combinations thereof. In embodiments, the position and angle of the ends of shaft 200 may be used to calculate the angular displacement between the ends and subsequently determine the reaction torque applied due to friction by analyzing the angular displacement at the ends of shaft 200. As the friction inducing surface 230 (i.e., referring to FIG. 2) applies a normal force to rotating rings 225 (i.e., referring to FIG. 2) coupled to shaft 200, the coefficient of friction of the drilling fluid present between the two may be determined by calculating the ratio between the force necessary to move the surface of rotating rings 225 horizontally over friction inducing surface 230 and the pressure between the two surfaces. As the lubricity is the measure of the reduction in friction and/or wear, other suitable parameters such as temperature, pressure, and/or combinations thereof may have an effect on lubricity. As such, those parameters may be adjusted within lubricity tester unit 100 to further analyze how lubricity is affected by downhole conditions.

Accordingly, this disclosure describes systems, methods, and apparatuses that may relate to measuring torque. The systems, methods, and apparatus may further be characterized by one or more of the following statements.

Statement 1. A lubricity tester unit, including: a housing; a shaft, wherein a first end of the shaft is disposed at a first end of the housing, wherein the shaft extends through housing along a central axis of the housing; an encoder, wherein the encoder is disposed on an internal wall of the housing, wherein the shaft is disposed through a hole in the encoder, wherein the encoder is an optical encoder configured to measure angular position of the shaft; rotating rings, wherein the rotating rings are coupled to a second end of the shaft; a friction inducing surface, wherein the friction inducing surface is disposed around the rotating rings; a first sensor, wherein the first sensor is disposed through the housing; and a second sensor, wherein the second sensor is disposed through the housing.

Statement 2. The lubricity tester unit of statement 1, further including a motor, a pulley, and a belt drive, wherein the motor, the pulley, and the belt drive are operable to rotate the shaft.

Statement 3. The lubricity tester unit of statement 2, wherein the pulley is disposed at the first end of the housing, wherein the belt drive couples the motor to the pulley, wherein the pulley further includes a protruding extension, wherein the first end of the shaft is fastened to the protruding extension.

Statement 4. The lubricity tester unit of any of the preceding statements, wherein a second end of the housing is disposed on an external base.

Statement 5. The lubricity tester unit of any of the preceding statements, further including a first flag, a sleeve, and a second flag.

Statement 6. The lubricity tester unit of statement 5, wherein the sleeve is disposed around the shaft, wherein the encoder is disposed between the sleeve and the first flag, wherein the second flag is disposed on an external surface of the sleeve.

Statement 7. The lubricity tester unit of statement 5, wherein the first sensor is an optical sensor, wherein the first sensor is horizontally aligned with the first flag, wherein the first sensor is configured to receive a measurement from the first flag, wherein the first flag includes a reflective surface.

Statement 8. The lubricity tester unit of statement 5, wherein the second sensor is an optical sensor, wherein the second sensor is horizontally aligned with the second flag, wherein the second sensor is configured to receive a measurement from the second flag, wherein the second flag includes a reflective surface.

Statement 9. The lubricity tester unit of any of the preceding statements, further including a friction inducing apparatus, wherein the friction inducing surface is disposed on the friction inducing apparatus, wherein the friction inducing apparatus is disposed about an internal portion of the housing, wherein the friction inducing apparatus includes an off-center axis in relation to the lubricity tester unit, wherein the friction inducing apparatus is configured to displace the friction inducing surface against the rotating rings.

Statement 10. The lubricity tester unit of statement 9, wherein the friction inducing apparatus further includes an internal chamber and a fluid pathway.

Statement 11. The lubricity tester unit of any of the preceding statements, further including: a motor; a pulley, wherein the pulley is disposed at the first end of the housing, wherein the pulley further includes a protruding extension, wherein the first end of the shaft is fastened to the protruding extension; a belt drive, wherein the belt drive couples the motor to the pulley; a first flag, wherein the first sensor is horizontally aligned with the first flag, wherein the first sensor is an optical sensor, wherein the first sensor is configured to receive a measurement from the first flag, wherein the first flag includes a reflective surface; a sleeve, wherein the sleeve is disposed around the shaft, wherein the encoder is disposed between the sleeve and the first flag; a second flag, wherein the second flag is disposed on an external surface of the sleeve, wherein the second sensor is horizontally aligned with the second flag, wherein the second sensor is an optical sensor, wherein the second sensor is configured to receive a measurement from the second flag, wherein the second flag includes a reflective surface; and a friction inducing apparatus, wherein the friction inducing surface is disposed on the friction inducing apparatus, wherein the friction inducing apparatus is disposed about an internal portion of the housing, wherein the friction inducing apparatus includes an off-center axis in relation to the lubricity tester unit, wherein the friction inducing apparatus is configured to displace the friction inducing surface against the rotating rings.

Statement 12. A method of measuring lubricity of a drilling fluid, including: disposing a sample of the drilling fluid in a housing of a lubricity tester unit; rotating a shaft, wherein a first end of the shaft is secured into a pulley disposed at a first end of the housing of the lubricity tester unit, wherein rotating rings are coupled to an opposing end of the shaft; applying a torque to the shaft; determining an angular displacement between the first end of the shaft and the opposing end of the shaft; and determining a coefficient of friction of the sample of the drilling fluid.

Statement 13. The method of statement 12, wherein applying the torque to the shaft includes actuating a friction inducing apparatus to displace an internal wall of a friction inducing surface to come into contact with the rotating rings.

Statement 14. The method of statement 12 or 13, further including measuring an angular position and a speed of the shaft with an encoder.

Statement 15. The method of statement 14, wherein the encoder is an optical encoder that is disposed about an internal wall of the housing and extends inward towards a central axis of the housing, wherein the shaft is disposed through a hole in the encoder.

Statement 16. The method of any one of statements 12 to 15, wherein the lubricity tester unit further includes a first flag and a first sensor, wherein the first flag is disposed on the shaft, wherein the first sensor is an optical sensor, wherein the first sensor is horizontally aligned with the first flag, wherein the first flag includes a reflective surface.

Statement 17. The method of statement 16, further including of: emitting a light from the first sensor; and receiving a reflected light from the first flag as the first flag rotates.

Statement 18. The method of any one of statements 12 to 17, wherein the lubricity tester unit further includes a second flag and a second sensor, wherein the second flag is disposed on the shaft, wherein the second sensor is an optical sensor, wherein the second sensor is horizontally aligned with the second flag, wherein the second flag includes a reflective surface.

Statement 19. The method of statement 18, further including of: emitting a light from the second sensor; and receiving a reflected light from the second flag as the second flag rotates.

Statement 20. The method of any one of statements 12 to 19, further including circulating the drilling fluid in a wellbore while drilling, and flowing the sample of the drilling fluid to the lubricity tester unit.

Statement 21. A downhole system, including: a drill string disposed in a wellbore; a lubricity tester unit disposed at a surface of the wellbore, wherein the lubricity tester unit includes: a housing; a shaft, wherein a first end of the shaft is disposed at a first end of the housing, wherein the shaft extends through housing along a central axis of the housing; an encoder, wherein the encoder is disposed on an internal wall of the housing, wherein the shaft is disposed through a hole in the encoder, wherein the encoder is an optical encoder configured to measure the angular position of the shaft; rotating rings, wherein the rotating rings are coupled to a second end of the shaft; a friction inducing surface, wherein the friction inducing surface is disposed around the rotating rings; a first sensor, wherein the first sensor is disposed through the housing; and a second sensor, wherein the second sensor is disposed through the housing; and an information handling system operable to measure angular displacement between the first end of the shaft and the second end of the shaft and to determine a coefficient of friction of the sample of a drilling fluid.

Statement 22. The drilling system of statement 21, wherein the information handling system is in wired or wireless communication with the lubricity tester unit.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only, and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A lubricity tester unit, comprising:
a housing;
a shaft, wherein a first end of the shaft is disposed at a first end of the housing, wherein the shaft extends through housing along a central axis of the housing;
an encoder, wherein the encoder is disposed on an internal wall of the housing, wherein the shaft is disposed through a hole in the encoder, wherein the encoder is an optical encoder configured to measure angular position of the shaft;
rotating rings, wherein the rotating rings are coupled to a second end of the shaft;
a friction inducing surface, wherein the friction inducing surface is disposed around the rotating rings;
a friction inducing apparatus, wherein the friction inducing surface is disposed on the friction inducing apparatus, wherein the friction inducing apparatus is disposed about an internal portion of the housing, wherein the friction inducing apparatus comprises an off-center axis in relation to the lubricity tester unit, wherein the friction inducing apparatus is configured to displace the friction inducing surface against the rotating rings;
a first sensor, wherein the first sensor is disposed through the housing; and
a second sensor, wherein the second sensor is disposed through the housing.

2. The lubricity tester unit of claim 1, further comprising a motor, a pulley, and a belt drive, wherein the motor, the pulley, and the belt drive are operable to rotate the shaft.

3. The lubricity tester unit of claim 2, wherein the pulley is disposed at the first end of the housing, wherein the belt drive couples the motor to the pulley, wherein the pulley further comprises a protruding extension, wherein the first end of the shaft is fastened to the protruding extension.

4. The lubricity tester unit of claim 1, wherein a second end of the housing is disposed on an external base.

5. The lubricity tester unit of claim 1, further comprising a first flag, a sleeve, and a second flag.

6. The lubricity tester unit of claim 5, wherein the sleeve is disposed around the shaft, wherein the encoder is disposed between the sleeve and the first flag, wherein the second flag is disposed on an external surface of the sleeve.

7. The lubricity tester unit of claim 5, wherein the first sensor is an optical sensor, wherein the first sensor is horizontally aligned with the first flag, wherein the first sensor is configured to receive a measurement from the first flag, wherein the first flag comprises a reflective surface.

8. The lubricity tester unit of claim 5, wherein the second sensor is an optical sensor, wherein the second sensor is horizontally aligned with the second flag, wherein the second sensor is configured to receive a measurement from the second flag, wherein the second flag comprises a reflective surface.

9. The lubricity tester unit of claim 1, wherein the friction inducing apparatus further comprises an internal chamber and a fluid pathway.

10. The lubricity tester unit of claim 1, further comprising:
a motor;
a pulley, wherein the pulley is disposed at the first end of the housing, wherein the pulley further comprises a protruding extension, wherein the first end of the shaft is fastened to the protruding extension;
a belt drive, wherein the belt drive couples the motor to the pulley;
a first flag, wherein the first sensor is horizontally aligned with the first flag, wherein the first sensor is an optical sensor, wherein the first sensor is configured to receive a measurement from the first flag, wherein the first flag comprises a reflective surface;
a sleeve, wherein the sleeve is disposed around the shaft, wherein the encoder is disposed between the sleeve and the first flag; and
a second flag, wherein the second flag is disposed on an external surface of the sleeve, wherein the second sensor is horizontally aligned with the second flag, wherein the second sensor is an optical sensor, wherein the second sensor is configured to receive a measurement from the second flag, wherein the second flag comprises a reflective surface.

11. A method of measuring lubricity of a drilling fluid, comprising:
disposing a sample of the drilling fluid in a housing of a lubricity tester unit;
rotating a shaft, wherein a first end of the shaft is secured into a pulley disposed at a first end of the housing of the lubricity tester unit, wherein rotating rings are coupled to an opposing end of the shaft;
applying a torque to the shaft;
actuating a friction inducing apparatus to displace an internal wall of a friction inducing surface to come into contact with the rotating rings, wherein the friction inducing surface is disposed on a friction inducing apparatus, wherein the friction inducing apparatus is disposed about an internal portion of the housing, wherein the friction inducing apparatus comprises an off-center axis in relation to the lubricity tester unit, wherein the friction inducing apparatus is configured to displace the friction inducing surface against the rotating rings;
determining an angular displacement between the first end of the shaft and the opposing end of the shaft; and
determining a coefficient of friction of the sample of the drilling fluid.

12. The method of claim 11, further comprising measuring an angular position and a speed of the shaft with an encoder.

13. The method of claim 12, wherein the encoder is an optical encoder that is disposed about an internal wall of the housing and extends inward towards a central axis of the housing, wherein the shaft is disposed through a hole in the encoder.

14. The method of claim 11, wherein the lubricity tester unit further comprises a first flag and a first sensor, wherein the first flag is disposed on the shaft, wherein the first sensor is an optical sensor, wherein the first sensor is horizontally aligned with the first flag, wherein the first flag comprises a reflective surface.

15. The method of claim 14, further comprising of:
emitting a light from the first sensor; and
receiving a reflected light from the first flag as the first flag rotates.

16. The method of claim 11, wherein the lubricity tester unit further comprises a second flag and a second sensor, wherein the second flag is disposed on the shaft, wherein the second sensor is an optical sensor, wherein the second sensor is horizontally aligned with the second flag, wherein the second flag comprises a reflective surface.

17. The method of claim 16, further comprising of:
emitting a light from the second sensor; and
receiving a reflected light from the second flag as the second flag rotates.

18. The method of claim 11, further comprising circulating the drilling fluid in a wellbore while drilling, and flowing the sample of the drilling fluid to the lubricity tester unit.

19. A downhole system, comprising:
a drill string disposed in a wellbore;
a lubricity tester unit disposed at a surface of the wellbore, wherein the lubricity tester unit comprises:
a housing;
a shaft, wherein a first end of the shaft is disposed at a first end of the housing, wherein the shaft extends through housing along a central axis of the housing;
an encoder, wherein the encoder is disposed on an internal wall of the housing, wherein the shaft is disposed through a hole in the encoder, wherein the encoder is an optical encoder configured to measure the angular position of the shaft;
rotating rings, wherein the rotating rings are coupled to a second end of the shaft;
a friction inducing surface, wherein the friction inducing surface is disposed around the rotating rings;
a friction inducing apparatus, wherein the friction inducing surface is disposed on the friction inducing apparatus, wherein the friction inducing apparatus is disposed about an internal portion of the housing, wherein the friction inducing apparatus comprises an off-center axis in relation to the lubricity tester unit, wherein the friction inducing apparatus is configured to displace the friction inducing surface against the rotating rings;
a first sensor, wherein the first sensor is disposed through the housing; and
a second sensor, wherein the second sensor is disposed through the housing; and
an information handling system operable to measure angular displacement between the first end of the shaft and the second end of the shaft and to determine a coefficient of friction of the sample of a drilling fluid.

20. The drilling system of claim 19, wherein the information handling system is in wired or wireless communication with the lubricity tester unit.

* * * * *